United States Patent
Pfister

[11] 4,208,423
[45] Jun. 17, 1980

[54] ANTICHOLINERGIC BRONCHODILATORS

[75] Inventor: Jürg R. Pfister, Los Altos, Calif.

[73] Assignee: Syntex Inc., Palo Alto, Calif.

[21] Appl. No.: 963,258

[22] Filed: Nov. 24, 1978

[51] Int. Cl.² ............... A61K 31/40; C07D 207/12
[52] U.S. Cl. ..................... 424/274; 260/326.38; 424/246; 424/248.55; 424/250; 424/256; 544/59; 544/144; 544/231; 546/20; 546/272
[58] Field of Search ............... 260/326.38; 424/274

[56] References Cited
U.S. PATENT DOCUMENTS

| | | | |
|---|---|---|---|
| 2,812,334 | 11/1957 | Moffett | 260/326.38 |
| 3,318,902 | 5/1967 | Freed et al. | 260/326.38 |

FOREIGN PATENT DOCUMENTS 2142809  6/1971  France ................... 424/274

*Primary Examiner*—Ethel G. Love
*Attorney, Agent, or Firm*—Tom M. Moran; Gerard A. Blaufarb

[57] ABSTRACT

Compounds of the formula

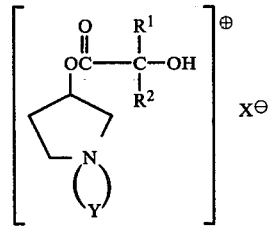

where $R^1$ and $R^2$ are the same or different and are $C_1$ to $C_6$ alkyl; $C_5$ or $C_6$ cycloalkyl; $C_5$ or $C_6$ cycloalkenyl; phenyl optionally substituted with a substitutent selected from the group $C_1$ to $C_6$ alkyl, $C_1$ to $C_6$ alkoxy and halo; or $C_4$ or $C_5$ heterocyclic aryl, the heteroatom selected from the group oxygen, nitrogen and sulfur; Y is the radical selected from $(CH_2)_n$, $(C_4H_8S)$, $(C_4H_8O)$ and

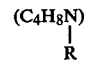

where R is hydrogen or $C_1$ to $C_6$ alkyl and n is the integer 4 or 5; and X is selected from the group methanesulfonate, benzenesulfonate, p-toluenesulfonate, nitrate, chloride, bromide and iodide. Methods for preparing these compounds are also disclosed. The compounds of the present invention are useful as anticholinergic agents.

7 Claims, No Drawings

ANTICHOLINERGIC BRONCHODILATORS

FIELD OF THE INVENTION

This invention relates to glycolic acid esters and pharmaceutically acceptable, non-toxic salts thereof and to methods for preparing these compounds. More particularly this invention relates to azoniaspiro glycolates, and to pharmaceutical compositions comprising one or more of the above compounds and to methods for achieving anticholinergic effects in mammals by using these compounds.

In summary, the compounds in accordance with the present invention can be represented by the following generic formula

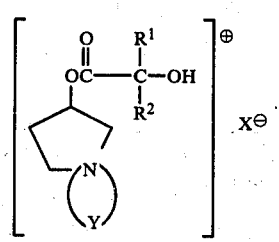

where $R^1$ and $R^2$ are the same or different and are $C_1$ to $C_6$ alkyl; $C_5$ or $C_6$ cycloalkyl; $C_5$ or $C_6$ cycloalkenyl; phenyl optionally substituted with a substituent selected from the group $C_1$ to $C_6$ alkyl, $C_1$ to $C_6$ alkoxy and halo; or $C_4$ or $C_5$ heterocyclic aryl, the heteroatom selected from the group oxygen, nitrogen and sulfur; Y is the radical selected from $(CH_2)_n$, $(C_4H_8S)$ and

where R is hydrogen or $C_1$ to $C_6$ alkyl and n is the integer 4 or 5; and X is selected from the group methanesulfonate, benzenesulfonate, p-toluenesulfonate, nitrate, chloride, bromide and iodide.

The process for preparing the compounds of the present invention of formula I comprises treating a compound of the formula

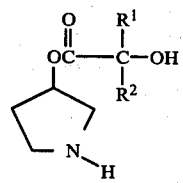

with Z—Y—Z, where Z are the groups methanesulfonyl, benzenesulfonyl, p-toluenesulfonyl, chloro, bromo or iodo, optionally with heat and catalyst.

The pharmaceutical compositions of the present invention include both solids or powders and solutions comprising one or more of the compounds of formula I in combination with a suitable pharmaceutical solvent or dispersant, i.e., sterile water or pharmaceutical solid excipients.

The compounds, compositions and methods of the present invention herein before disclosed will become more readily apparent from the following description.

DESCRIPTION OF THE PREFERRED EMBODIMENTS

The compounds of the present invention of formula I are subgenerically represented by the formulas described below.

1.

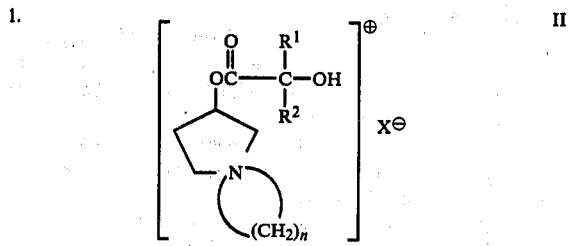

where $R^1$ and $R^2$ are the same or different and are $C_1$ to $C_6$ alkyl; $C_5$ to $C_6$ cycloalkyl; $C_5$ to $C_6$ cycloalkenyl; phenyl optionally substituted with a substituent selected from the group $C_1$ to $C_6$ alkyl, $C_1$ to $C_6$ alkoxy and halo; or $C_4$ or $C_5$ heterocyclic aryl, the heteroatom selected from the group oxygen, nitrogen and sulfur; X is selected from the group methanesulfonate, benzenesulfonate, p-toluenesulfonate, chloride, bromide and iodide; and n is the integer 4 or 5.

In the compounds of the present invention of formula II $R^1$ and $R^2$ are the same or different and are preferably $C_1$ to $C_4$ alkyl, cyclopentyl, cyclohexyl, cyclopent-2-enyl, cyclohex-3-enyl, phenyl optionally substituted with a substituent selected from the group $C_1$ to $C_4$ alkyl, $C_1$ to $C_4$ alkoxy, chloro and bromo, or thienyl and X is selected from the group methanesulfonate, benzenesulfonate, chloride and bromide.

Most preferred compounds of formula II are those where $R^1$ and $R^2$ are the same or different and are methyl, ethyl, cyclopentyl, cyclohexyl, phenyl or thienyl and X is chloride or bromide.

Particularly preferred compounds of formula II are:
2-(2,2-diphenyl-2-hydroxyacetoxy)-5-azoniaspiro[4.4-]nonane chloride;
2-(2,2-diphenyl-2-hydroxyacetoxy)-5-azoniaspiro[4.5]-decane chloride;
2-(2-cyclopentyl-2-hydroxy-2-phenylacetoxy)-5-azoniaspiro[4.4]nonane chloride; and
2-(2-cyclopentyl-2-hydroxy-2-phenylacetoxy)-5-azoniaspiro[4.4]nonane bromide.

2.

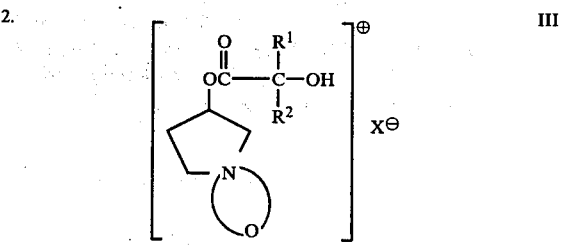

wherein $R^1$ and $R^2$ are the same or different and are $C_1$ to $C_6$ alkyl; $C_5$ to $C_6$ cycloalkyl; $C_5$ to $C_6$ cycloalkenyl; phenyl optionally substituted with a substituent selected from the group $C_1$ to $C_6$ alkyl, $C_1$ to $C_6$ alkoxy and halo; or $C_4$ or $C_5$ heterocyclic aryl, the heteroatom selected from the group oxygen, nitrogen and sulfur; X is selected from the group methanesulfonate, benzenesulfonate, p-toluenesulfonate, nitrate, chloride, bromide and iodide.

In the compounds of the present invention of formula III R¹ and R² are the same or different and are preferably $C_1$ to $C_4$ alkyl, cyclopentyl, cyclohexyl, cyclopent-2-enyl, cyclohex-3-enyl, phenyl optionally substituted with a substituent selected from the group $C_1$ to $C_4$ alkyl, $C_1$ to $C_4$ alkoxy, chloro and bromo, or thienyl and X is selected from the group nitrate, methanesulfonate, chloride and bromide.

Most preferred compounds of formula III are those where R¹ and R² are the same or different and are methyl, cyclopentyl, cyclohexyl, phenyl or thienyl and X is chloride or bromide.

Particularly preferred compounds of formula III are:
2-(2,2-diphenyl-2-hydroxyacetoxy)-8-oxa-5-azoniaspiro[4.5]decane chloride;
2-(2-cyclopentyl-2-hydroxy-2-phenylacetoxy)-8-oxa-5-azoniaspiro[4.5]decane chloride; and
2-(2-cyclopentyl-2-hydroxy-2-phenylacetoxy)-8-oxa-5-azoniaspiro[4.5]decane bromide.

3. 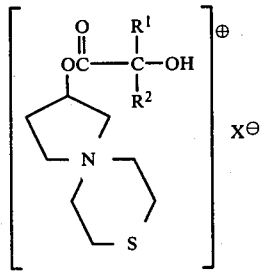 IV wherein R¹ and R² are the same or different and are $C_1$ to $C_6$ alkyl; $C_5$ to $C_6$ cycloalkyl; $C_5$ to $C_6$ cycloalkenyl; phenyl optionally substituted with a substituent selected from the group $C_1$ to $C_6$ alkyl, $C_1$ to $C_6$ alkoxy and halo; or $C_4$ or $C_5$ heterocyclic aryl, the heteroatom selected from the group oxygen, nitrogen and sulfur; X is selected from the group methanesulfonate, benzenesulfonate, p-toluenesulfonate, chloride, bromide and iodide.

In the compounds of the present invention of formula III R¹ and R² are the same or different and are preferably $C_1$ to $C_4$ alkyl, cyclopentyl, cyclohexyl, cyclopent-2-enyl, cyclohex-3-enyl, phenyl optionally substituted with a substituent selected from the group $C_2$ to $C_4$ alkyl, $C_1$ to $C_4$ alkoxy, chloro and bromo, or thienyl and X is selected from the group methanesulfonate, benzenesulfonate, chloride and bromide.

Most preferred compounds of formula IV are those where R¹ and R² are the same or different and are i-propyl, cyclopentyl, cyclohexyl, phenyl or thienyl and X is bromide, iodide or methanesulfonate.

Particularly preferred compounds of formula IV are:
2-(2,2-diphenyl-2-hydroxyacetoxy)-8-thia-5-azoniaspiro[4.5]decane bromide;
2-(2-hydroxy-2-isopropyl-2-phenylacetoxy)-8-thia-5-azoniaspiro[4.5]decane iodide; and
2-(2-cyclopentyl-2-hydroxy-2-phenylacetoxy)-8-thia-5-azoniaspiro[4.5]decane methanesulfonate.

4. 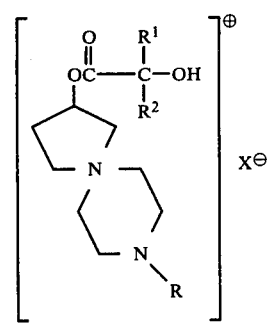 V wherein R¹ and R² are the same or different and are $C_1$ to $C_6$ alkyl; $C_5$ to $C_6$ cycloalkyl; $C_5$ to $C_6$ cycloalkenyl; phenyl optionally substituted with a substituent selected from the group $C_1$ to $C_6$ alkyl, $C_1$ to $C_6$ alkoxy and halo; or $C_4$ or $C_5$ heterocyclic aryl, the heteroatom selected from the group oxygen, nitrogen and sulfur; X is selected from the group methanesulfonate, benzenesulfonate, p-toluenesulfonate, chloride, bromide and iodide; and R is hydrogen or $C_1$ to $C_6$ alkyl.

In the compounds of the present invention of formula V R¹ and R² are the same or different and are preferably $C_1$ to $C_4$ alkyl, cyclopentyl, cyclohexyl, cyclopent-2-enyl, cyclohex-3-enyl, phenyl optionally substituted with a substituent selected from the group $C_1$ to $C_4$ alkyl, $C_1$ to $C_4$ alkoxy, chloro and bromo, or thienyl and X is selected from the group methanesulfonate, benzenesulfonate, chloride and bromide.

Most preferred compounds of formula V are those where R¹ and R² are the same or different and are i-propyl, cyclopentyl, cyclohexyl, phenyl or thienyl and X is bromide, iodide or methanesulfonate.

Particularly preferred compounds of formula V are the following:
2-(2,2-diphenyl-2-hydroxyacetoxy)-8-aza-8-methyl-5-azoniaspiro[4.5]decane bromide;
2-(2-hydroxy-2-isopropyl-2-phenylacetoxy)-8-aza-8-methyl-5-azoniaspiro[4.5]decane iodide; and
2-(2-cyclohexyl-2-hydroxy-2-phenylacetoxy)-8-aza-8-methyl-5-azoniaspiro[4.5]decane methanesulfonate.

The compounds of the present invention of formula I are made by the following process depicted schematically:

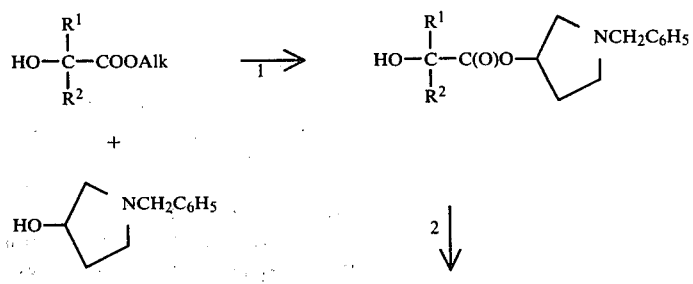

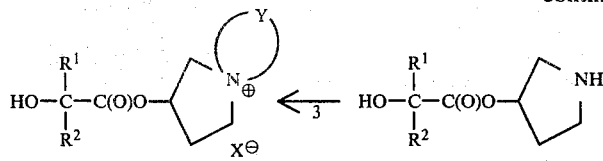

The initial reaction, as shown in reaction step 1 involves the transesterification of 1-benzyl-3-pyrrolidinol with an alkyl ester of $R^1$, $R^2$-glycolic acid. As depicted in this step, ALK can be any lower alkyl group including methyl, ethyl, i-propyl, and the like. While the benzyl pyrrolidinol compound is the preferred starting material in this step, any of the prior art groups generally known as protecting groups can be employed as the substituent at the nitrogen atom. These include, for example, the groups diphenylmethyl, o-nitrobenzyl, p-nitrobenzyl, 3,5-dinitrobenzyl, p-methoxybenzyl, pivaloyloxymethyl, trichloroethyloxycarbonyl and the like. The transesterification is conducted in the presence of strong base, for example an alkali metal hydride, optionally in the presence of inert organic solvent, at times and temperatures sufficient to complete the reaction, typically 30 minutes to 24 hours at 50° to 150°, preferably 4 hours under reflux conditions, e.g., 100°. Solvents for this reaction include the aliphatic hydrocarbon solvents, such as hexane, heptane, octane, etc.; and the aromatic solvents such as benzene toluene, etc.

The glycolic acid ester, preferably isolated from step 1 is subjected to hydrogenolysis to remove the protecting group on the nitrogen atom. Preferably the reaction is conducted in aqueous acid solutions, most preferably at a pH of about 4 in the presence of a hydrogenolysis catalyst for a time sufficient to assure completeness of the reaction. Various metal catalysts known in the art can be employed in this step such including platinum, Raney nickel, etc. Typically the catalyst is palladium optionally on a substrate, e.g., carbon, aluminum oxide, barium sulfate, etc. The catalyst is most preferably palladium oxide or palladium black. The reaction is conducted at about room temperature and terminated when complete, i.e., after hydrogen uptake has ceased.

Formation of the spiro compounds of formula II can be accomplished by treatment of the reaction intermediate of step 2 with an alkylene dihalide such as 1,4-dibromobutane, 1,4-dichlorobutane, 1,5-dichloropentane and the like or with an alkylene ditosylate or dimesylate in a suitable inert organic solvent in the presence of a base. Preferably the alkylene dihalides are employed in reaction step 3, most preferably the alkylene dibromides with the base being preferably an organic base such as a trialkylamine, e.g., tertiary amine, or a heteroaliphatic amine, e.g., N-methylmorpholine, quinuclidine, etc. The reaction solvent is typically an inert polar organic solvent such as acetonitrile, dimethylsulfoxide, dimethylformamide, and the like, the reaction being conducted for a time and at a temperature sufficient to assure completeness of reaction, typically 75°–150°, for 24 to 72 hours.

Formation of the spiro compounds of formulas III, IV and V may be effected under identical conditions and with identical solvents as set forth above. However, rather than using the 1,4- or 1,5-disubstituted alkanes, disubstituted alkylethers, disubstituted alkyl thioethers or disubstituted alkyl tertiary amines are employed. For example, in the preparation of the compounds of formula III, the product of reaction step 2 is treated with a di(haloethyl)ether, preferably 2,2'-dichloroethyl ether; in the preparation of the compounds of formula IV, the product of reaction step 2 is treated with a di(haloethyl)thioether, preferably 2,2'-dichloroethyl thioether; and in the preparation of the compounds of formula V, the product of reaction step 2 is treated with a di(haloethyl)tertiary amine, preferably 2,2'-dichloroethylmethylamine.

The compounds of the invention are predominantly antagonists of acetyl choline and are particularly effective as bronchodilators. As such, the compounds of this invention are typically administered in dosages of about from 0.01 to 5 mg per kg. of body weight. The precise effective dosage will, of course, vary depending upon the mode of administration, the condition being treated, and the host. Where the compounds are used as pulmonary anticholinergics in mammals they are typically administered either orally, intravenously, or by inhalation.

The compounds of the present invention can be administered in a wide variety of dosage forms, either alone or in combination with other pharmaceutically compatible medicaments, in the form of pharmaceutical compositions suited for oral, parenteral or aerosol administration. The compounds are typically administered as pharmaceutical compositions consisting essentially of the compounds of the invention and a pharmaceutical carrier. The pharmaceutical carriers can be either a solid material or a liquid in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, pharmaceutical phosphate salts and the like.

The liquid compositions can, for example, be in the form of solutions, emulsions, suspensions, syrups, or elixirs and optionally can contain small quantities of preservatives and/or buffering agents, and preferably contain the therapeutic agents in convenient unit dosage.

The solid compositions can take the form of tablets, powders, capsules, pills and the like, preferably in unit dosage forms for simple administration or precise dosages. Suitable solid carriers include, for example, pharmaceutical grades of starch, lactose, sodium saccharine, sodium bisulfite and the like.

Also based on studies on related compounds, it can be predicted that a number of the present compounds will exhibit useful anticholinergic activity when administered topically, intradermally, or subcutaneously.

The compounds of formula I can be administered as racemic mixtures or they can be administered as resolved enantiomers or optical isomers. In some instances, one enantiomer or optical isomer exhibits a greater anticholinergic effect than does the other corresponding enantiomer or optical isomer.

As used in the specification and the appended claims, the following terms have the meaning indicated. The term "$C_1$ to $C_6$ alkyl" refers to a straight or branched chain, monovalent substituent consisting solely of carbon and hydrogen, containing no unsaturation, and having from 1 to 6 carbon atoms. Examples of such alkyl groups are methyl, ethyl, n-propyl, i-propyl, n-butyl, t-butyl, n-hexyl, 2-methylpentyl and the like. The term "$C_1$ to $C_6$ alkoxy" refers to the above disclosed alkyl groups linked through an ether linkage, having the free valence from the ether oxygen. Examples of such groups include methoxy, ethoxy, n-propoxy, i-propoxy, n-butoxy, t-butoxy, n-hexyloxy, and the like. The term "$C_5$ to $C_6$ cycloalkyl" refers to a 5 or 6 membered monovalent ring containing only hydrogen and carbon that is fully saturated such as exemplified by cyclopentyl or cyclohexyl. "$C_5$ to $C_6$ cycloalkenyl" differs from the above cycloalkyl by having in the ring at least one unsaturated site. Such includes 1-, 2- or 3-cyclopentenyl, 1-, 2-, or 3-cyclohexenyl, 1,4-cyclohexadienyl, 1,3-cyclopentadienyl, and the like. The term "halide" refers to fluoride, chloride, bromide and iodide. The term "heterocyclic aryl, the heteroatom selected from oxygen, nitrogen and sulfur" is intended to mean the monovalent heterocyclic radicals of aromatic character containing, in addition to the heteroatom, 4 or 5 carbon atoms in the ring. Examples of these radicals are pyrryl, for example 2- or 3-pyrryl, pyridyl, for example 2-, 3- or 4-pyridyl, thienyl, for example 2- or 3-thienyl and furyl, for example 2-furyl or 3-furyl. "Phenyl optionally substituted with a substituent selected from the group $C_1$ to $C_6$ alkyl, $C_1$ to $C_6$ alkoxy and halo" is intended to include unsubstituted phenyl, monosubstituted phenyl and polysubstituted phenyl. Such include methylphenyl, for example 2- or 3-methylphenyl, dimethylphenyl, for example 2,4- or 3,5-dimethylphenyl, methoxyphenyl, for example 2- or 3-methoxyphenyl, dimethoxyphenyl for example 2,4- or 3,5-dimethoxyphenyl, halophenyl for example 4-chlorophenyl, or 4-bromophenyl, or dihalophenyl, for example 2,4-dichlorophenyl or 2,4-dibromophenyl.

The compounds of formula I may possess a chiral center. Accordingly, the compounds of the invention may be prepared in either their optically active form or as a racemic mixture. Unless otherwise specified, the compounds described herein are all in the racemic form. However, the scope of the subject invention is not to be considered limited to the racemic, form, but to encompass the individual optical isomers of the compounds of the present invention.

Where desired the individual diastereomeric and optically isomeric compounds can be isolated by conventional separation and purification procedures in the case of diastereomers and by conventional resolution procedures in the case of optical isomers. Optimum physical or physical-chemical, separation procedures and resolution procedures can be obtained by routine trial and error procedures well within the scope of those skilled in the art.

A further understanding of the invention can be had from the following non-limiting Preparations and Examples. As used hereinabove and below unless expressly stated to the contrary, all temperatures and temperature ranges refer to the centrigrade system and the terms ambient or room temperature refer to about 20° C. The term percent or (%) refers to weight percent and the term mole and moles refers to gram moles. The term equivalent refers to a quantity of reagent equal in moles to the moles of the preceding or succeeding reactant recited in that Preparation or Example in the terms of moles of finite weight or volume. As noted earlier, compounds having asymmetric centers and optical activity are isolated in their racemic form ($\pm$) unless otherwise indicated.

PREPARATION 1

To a solution of 12 g methyl benzilate and 8.2 g 1-benzyl-3-pyrrolidinol in 200 ml n-heptane is added 100 mg sodium hydride and the mixture refluxed for 4 hours, separating the methanol formed in a Dean-Stark separator. The cooled organic phase is washed with water and then extracted with 2N HCl. The aqueous phase is made alkaline with solid $K_2CO_3$ and extracted with ether to give 1-benzyl-3-(2,2-diphenyl-2-hydroxyacetoxy)pyrrolidine as an oil (18.2 g).

In a similar manner, using the following compounds in place of methyl benzilate:
methyl dimethylglycolate;
methyl diethylglycolate;
methyl di-n-butylglycolate;
methyl methyl-n-butylglycolate;
ethyl methylcyclopentylglycolate;
ethyl dicyclopentylglycolate;
ethyl methylcyclopent-2-enylglycolate;
ethyl methylpentylglycolate;
methyl methyl(3-methylphenyl)glycolate;
methyl methyl(4-chlorophenyl)glycolate;
methyl methylpyrrol-3-ylglycolate;
methyl methylfur-2-ylglycolate; and
methyl methylthien-2-ylglycolate,
are prepared the following compounds:
1-benzyl-3-(2,2-dimethyl-2-hydroxyacetoxy)pyrrolidine;
1-benzyl-3-(2,2-diethyl-2-hydroxyacetoxy)pyrrolidine;
1-benzyl-3-(2,2-di-n-butyl-2-hydroxyacetoxy)pyrrolidine;
1-benzyl-3-(2-methyl-2-n-butyl-2-hydroxyacetoxy)pyrrolidine;
1-benzyl-3-(2-methyl-2-cyclopentyl-2-hydroxyacetoxy)pyrrolidine;
1-benzyl-3-(2,2-dicyclopentyl)-2-hydroxyacetoxy)pyrrolidine;
1-benzyl-3-[2-methyl-2-(cyclopent-2-enyl)-2-hydroxyacetoxy]pyrrolidine;
1-benzyl-3-(2-methyl-2-phenyl-2-hydroxyacetoxy)pyrrolidine;
1-benzyl-3-[2-methyl-2-(3-methylphenyl)-2-hydroxyacetoxy]pyrrolidine;
1-benzyl-3-[2-methyl-2-(4-chlorophenyl)-2-hydroxyacetoxy]pyrrolidine;
1-benzyl-3-[2-methyl-2-(pyrrol-3-yl)-2-hydroxyacetoxy]pyrrolidine;
1-benzyl-3-[2-methyl-2-(fur-2-yl)-2-hydroxyacetoxy]pyrrolidine; and
1-benzyl-3-[2-methyl-2-(thien-2-yl)-2-hydroxyacetoxy]pyrrolidine;
1-benzyl-3-(2,2-diphenyl-2-hydroxyacetoxy)pyrrolidine.

PREPARATION 2

18.2 g of the amino ester of Preparation 1 is dissolved in 900 ml ethanol, and sufficient ethanolic hydrochloric acid is added to obtain a pH of about 4. The resulting solution is hydrogenated over 2.2 g 10% palladium on carbon at normal pressure and room temperature. After hydrogen uptake has ceased (about 1.2 l), the solution is filtered through Celite and the filtrate concentrated to about 100 ml on a rotary evaporator. The residue is diluted with 500 ml water, made alkaline with solid potassium carbonate, and extracted with ether to give 12.4 g of 3-(2,2-diphenyl-2-hydroxyacetoxy)pyrrolidine, an oil which can be crystallized from ether/hexane. mp. 123°–124°.

In a similar manner, the benzylpyrrolidines of Preparation I are converted into their respective pyrrolidines.

EXAMPLE 1

A solution of 12.4 g of the secondary amine of Preparation 2, 11 g of 1,4-dichlorobutane and 8 ml of triethylamine in 180 ml acetonitrile is refluxed for 48 hours. The cooled reaction mixture is evaporated to dryness, the residue dissolved in 350 ml water and extracted with ether. The aqueous phase is extracted continuously with ethyl acetate for 48 hours to give 8.3 g of 2-(2,2-diphenyl-2-hydroxyacetoxy)-5-azoniaspiro[4.4]nonane chloride, mp 150°–152° (from MeOH/AcOEt).

In a similar manner the pyrrolidines illustrated in Preparation 2 are converted into the following compounds:

2-(2,2-dimethyl-2-hydroxyacetoxy)-5-azoniaspiro[4.4]nonane chloride;
2-(2,2-dimethyl-2-hydroxyacetoxy)-5-azoniaspiro[4.5]decane bromide;
2-(2,2-diethyl-2-hydroxyacetoxy)-5-azoniaspiro[4.4]nonane chloride;
2-(2,2-diethyl-2-hydroxyacetoxy)-5-azoniaspiro[4.5]decane bromide;
2-(2,2-di-n-butyl-2-hydroxyacetoxy)-5-azoniaspiro[4.4]nonane chloride;
2-(2,2-di-n-butyl-2-hydroxyacetoxy)-5-azoniaspiro[4.5]decane bromide;
2-(2-methyl-2-n-butyl-2-hydroxyacetoxy)-5-azoniaspiro[4.4]nonane chloride;
2-(2-methyl-2-n-butyl-2-hydroxyacetoxy)-5-azoniaspiro[4.5]decane bromide;
2-(2-methyl-2-cyclopentyl-2-hydroxyacetoxy)-5-azoniaspiro[4.4]nonane chloride;
2-(2-methyl-2-cyclopentyl-2-hydroxyacetoxy)-5-azoniaspiro[4.5]decane bromide;
2-(2,2-dicyclopentyl-2-hydroxyacetoxy)-5-azoniaspiro[4.4]nonane chloride;
2-(2,2-dicyclopentyl-2-hydroxyacetoxy)-5-azoniaspiro[4.5]decane bromide;
2-[2-methyl-2-(cyclopent-2'-enyl)-2-hydroxyacetoxy]-5-azoniaspiro[4.4]nonane chloride;
2-[2-methyl-2-(cyclopent-2'-enyl)-2-hydroxyacetoxy]-5-azoniaspiro[4.5]decane bromide;
2-(2-methyl-2-phenyl-2-hydroxyacetoxy)-5-azoniaspiro[4.4]nonane chloride;
2-(2-methyl-2-phenyl-2-hydroxyacetoxy)-5-azoniaspiro[4.5]decane bromide;
2-[2-methyl-2-(3-methylphenyl)-2-hydroxyacetoxy]-5-azoniaspiro[4.4]nonane chloride;
2-[2-methyl-2-(3-methylphenyl)-2-hydroxyacetoxy]-5-azoniaspiro[4.5]decane bromide;
2-[2-methyl-2-(4-chlorophenyl)-2-hydroxyacetoxy]-5-azoniaspiro[4.4]nonane chloride;
2-[2-methyl-2-(4-chlorophenyl)-2-hydroxyacetoxy]-5-azoniaspiro[4.5]decane bromide;
2-[2-methyl-2-(pyrrol-3-yl)-2-hydroxyacetoxy]-5-azoniaspiro[4.4]nonane chloride;
2-[2-methyl-2-(pyrrol-3-yl)-2-hydroxyacetoxy]-5-azoniaspiro[4.5]decane bromide;
2-[2-methyl-2-(fur-2-yl)-2-hydroxyacetoxy]-5-azoniaspiro[4.4]nonane chloride;
2-[2-methyl-2-(fur-2-yl)-2-hydroxyacetoxy]-5-azoniaspiro[4.5]decane bromide;
2-[2-methyl-2-(thien-2-yl)-2-hydroxyacetoxy]-5-azoniaspiro[4.4]nonane chloride;
2-[2-methyl-2-(thien-2-yl)-2-hydroxyacetoxy]-5-azoniaspiro[4.5]decane bromide; and
2-(2,2-diphenyl-2-hydroxyacetoxy)-5-azoniaspiro[4.5]decane chloride, mp 237°–238°.

EXAMPLE 2

A solution of 2.2 g of the secondary amine of Preparation 2, 2.2 g of 2,2'-dichloroethyl ether, and 1.0 g of triethylamine in 40 ml acetonitrile is refluxed for 72 hours. The crystalline material that deposits on cooling is filtered off, washed with a little acetone, and recrystallized from isopropanol affording 2-(2,2-diphenyl-2-hydroxyacetoxy)-8-oxa-5azoniaspiro[4.5]decane chloride, 2.1 g, mp. 266°–267°.

In a similar manner, the pyrrolidines illustrated in Preparation 2 are converted into the following compounds:

(by reaction with 2,2'-dichloroethyl ether)
2-(2,2-dimethyl-2-hydroxyacetoxy)-8-oxa-5-azoniaspiro[4.5]decane chloride;
2-(2,2-dicyclopentyl-2-hydroxyacetoxy)-8-oxa-5-azoniaspiro[4.5]decane chloride;
2-(2-methyl-2-cyclopentyl-2-hydroxyacetoxy)-8-oxa-5-azoniaspiro[4.5]decane chloride;
2-[2-methyl-2-(cyclopent-2-enyl)-2-hydroxyacetoxy]-8-oxa-5-azoniaspiro[4.5]decane chloride;
2-(2-methyl-2-phenyl-2-hydroxyacetoxy)-8-oxa-5-azoniaspiro[4.5]decane chloride;
2-[2-methyl-2-(3-methylphenyl)-2-hydroxyacetoxy]-8-oxa-5-azoniaspiro[4.5]decane chloride;
2-[2-methyl-2-(4-chlorophenyl)-2-hydroxyacetoxy]-8-oxa-5-azoniaspiro[4.5]decane chloride;
2-[2-methyl-2-(pyrrol-3'-yl)-2-hydroxyacetoxy]-8-oxa-5-azoniaspiro[4.5]decane chloride;
2-[2-methyl-2-(fur-2'-yl)-2-hydroxyacetoxy]-8-oxa-5-azoniaspiro[4.5]decane chloride; and
2-[2-methyl-2-(thien-2'-yl)-2-hydroxyacetoxy]-8-oxa-5-azoniaspiro[4.5]decane chloride.

(by reaction with 2,2'-dichloroethyl thioether)
2-(2,2-dimethyl-2-hydroxyacetoxy)-8-thia-5-azoniaspiro[4.5]-decane chloride;
2-(2,2-dicyclopentyl-2-hydroxyacetoxy)-8-thia-5-azoniaspiro[4.5]-decane chloride;
2-(2-methyl-2-cyclopentyl-2-hydroxyacetoxy)-8-thia-5-azoniaspiro[4.5]decane chloride;
2-[2-methyl-2-(cyclopent-2'-enyl)-2-hydroxyacetoxy]-8-thia-5-azoniaspiro[4.5]decane chloride;
2-(2-methyl-2-phenyl-2-hydroxyacetoxy)-8-thia-5-azoniaspiro[4.5]decane chloride;
2-[2-methyl-2-(3-methylphenyl)-2-hydroxyacetoxy]-8-thia-5-azoniaspiro[4.5]decane chloride;
2-[2-methyl-2-(4-chlorophenyl)-2-hydroxyacetoxy]-8-thia-5-azoniaspiro[4.5]decane chloride;
2-[2-methyl-2-(pyrrol-3-yl)-2-hydroxyacetoxy]-8-thia-5-azoniaspiro[4.5]decane chloride;
2-2-methyl-2-(fur-2-yl)-2-hydroxyacetoxy]-8-thia-5-azoniaspiro[4.5]decane chloride; and
2-[2-methyl-2-(thien-2-yl)-2-hydroxyacetoxy]-8-thia-5-azoniaspiro[4.5]decane chloride.

(by reaction with 2,2'-dichloroethylmethylamine)
2-(2,2-dimethyl-2-hydroxyacetoxy)-8-aza-8-methyl-5-azoniaspiro[4.5]-decane chloride;

2-(2,2-dicyclopentyl-2-hydroxyacetoxy)-8-aza-8-methyl-5-azoniaspiro[4.5]-decane chloride;
2-(2-methyl-2-cyclopentyl-2-hydroxyacetoxy)-8-aza-8-methyl-5-azoniaspiro[4.5]decane chloride;
2-[2-methyl-2-(cyclopent-2-enyl)-2-hydroxyacetoxy]-8-aza-8-methyl-5-azoniaspiro[4.5]decane chloride;
2-(2-methyl-2-phenyl-2-hydroxyacetoxy)-8-aza-8-methyl-5-azoniaspiro[4.5]decane chloride;
2-[2-methyl-2-(3-methylphenyl)-2-hydroxyacetoxy]-8-aza-8-methyl-5-azoniaspiro[4.5]decane chloride;
2-[2-methyl-2-(4-chlorophenyl)-2-hydroxyacetoxy]-8-aza-8-methyl-5-azoniaspiro[4.5]decane chloride;
2-[2-methyl-2-(pyrrol-3-yl)-2-hydroxyacetoxy]-8-aza-8-methyl-5-azoniaspiro[4.5]decane chloride;
2-[2-methyl-2-(fur-2'-yl)-2-hydroxyacetoxy]-8-aza-8-methyl-5-azoniaspiro[4.5]decane chloride; and
2-[2-methyl-2-(thien-2'-yl)-2-hydroxyacetoxy]-8-aza-8-methyl-5-azoniaspiro[4.5]decane chloride.

While the present invention has been described with reference to specific embodiments thereof, it should be understood by those skilled in the art that various changes may be made and equivalents may be substituted without departing from the true spirit and scope of the invention. In addition, many modifications can be made to adapt a particular situation, material or composition of matter, process, process step or steps or objective to the spirit of this invention without departing from its essential teachings.

I claim:

1. Compounds of the formula

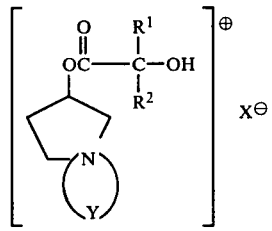

where $R^1$ and $R^2$ are the same or different and are $C_1$ to $C_6$ alkyl; $C_5$ or $C_6$ cycloalkyl; $C_5$ or $C_6$ cycloalkenyl; phenyl optionally substituted with a substituent selected from the group $C_1$ to $C_6$ alkyl, $C_1$ to $C_6$ alkoxy and halo; or monovalent heterocyclic radical of aromatic character containing a heteroatom selected from oxygen, nitrogen and sulfur and, in addition to the heteroatom, 4 or 5 carbons in the ring; Y is the radical selected from $(CH_2)_n$, and n is the integer 4; and X is selected from the group nitrate, methanesulfonate, benzenesulfonate, p-toluenesulfonate, chloride, bromide and iodide.

2. The compounds in accordance with claim 1 having the formula

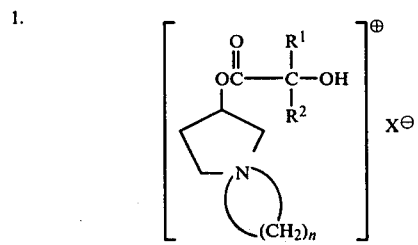

where $R^1$ and $R^2$ are the same or different and are $C_1$ to $C_6$ alkyl; $C_5$ to $C_6$ cycloalkyl; $C_5$ to $C_6$ cycloalkenyl; phenyl optionally substituted with a substituent selected from the group $C_1$ to $C_6$ alkyl, $C_1$ to $C_6$ alkoxy and halo; or monovalent heterocyclic radical of aromatic character containing a heteroatom selected from oxygen, nitrogen and sulfur and, in addition to the heteroatom, 4 or 5 carbons in the ring; X is selected from the group methanesulfonate, benzenesulfonate, p-toluenesulfonate, chloride, bromide and iodide; and n is the integer 4.

3. The compounds in accordance with claim 2 wherein $R^1$ and $R^2$ are the same or different and are $C_1$ to $C_4$ alkyl, cyclopentyl, cyclohexyl, cyclopent-2-enyl, cyclohex-3-enyl, phenyl optionally substituted with a substituent selected from the group $C_1$ to $C_4$ alkyl, $C_1$ to $C_4$ alkoxy, chloro and bromo, or thienyl and X is selected from the group methanesulfonate, benzenesulfonate, chloride and bromide.

4. The compounds in accordance with claim 3 wherein $R^1$ and $R^2$ are the same or different and are methyl, ethyl, cyclopentyl, cyclohexyl, phenyl or thienyl and X is chloride or bromide.

5. The compounds in accordance with claim 4 wherein $R^1$ is the same as $R^2$ and is phenyl, and X is chloride.

6. An anticholinergic composition which comprises a pharmaceutical carrier and an anti-cholinergic effective amount of at least one compound selected from the group represented by the formula

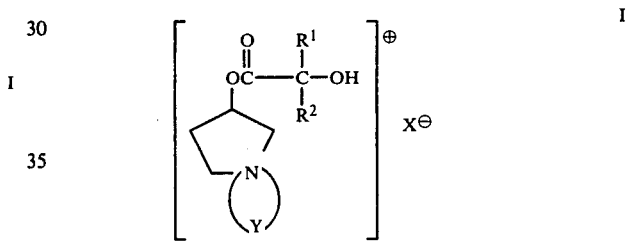

where $R^1$ and $R^2$ are the same or different and are $C_1$ to $C_6$ alkyl; $C_5$ or $C_6$ cycloalkyl; $C_5$ or $C_6$ cycloalkenyl; phenyl optionally substituted with a substituent selected from the group $C_1$ to $C_6$ alkyl, $C_1$ to $C_6$ alkoxy and halo; or; monovalent heterocyclic radical of aromatic character containing a heteroatom selected from oxygen, nitrogen and sulfur and, in addition to the heteroatom, 4 or 5 carbons in the ring; Y is the radical selected from $(CH_2)_n$ and n is the integer 4; and X is selected from the group methanesulfonate, benzenesulfonate, p-toluenesulfonate, nitrate, chloride, bromide and iodide.

7. A method for effecting bronchodilation in mammals which comprises administering to said mammals a bronchodilating effective amount of compounds of the formula

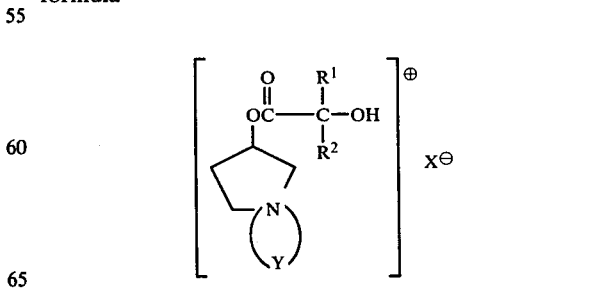

where $R^1$ and $R^2$ are the same or different and are $C_1$ to $C_6$ alkyl; $C_5$ or $C_6$ cycloalkyl; $C_5$ or $C_6$ cycloalkenyl;

phenyl optionally substituted with a substituent selected from the group $C_1$ to $C_6$ alkyl, $C_1$ to $C_6$ alkoxy and halo; or monovalent heterocyclic radical of aromatic character containing a heteroatom selected from oxygen, nitrogen and sulfur, and in addition to the heteroatom, 4 or 5 carbons in the ring; Y is the radical selected from $(CH_2)_n$ and n is the integer 4; and X is selected from the group methanesulfonate, benzenesulfonate, p-toluenesulfonate, nitrate, chloride, bromide and iodide.

* * * * *